(12) United States Patent
Fisher

(10) Patent No.: US 11,386,550 B2
(45) Date of Patent: Jul. 12, 2022

(54) METHODS FOR IMPROVED MEASUREMENTS OF BRAIN VOLUME AND CHANGES IN BRAIN VOLUME

(71) Applicant: BIOGEN MA INC., Cambridge, MA (US)

(72) Inventor: Elizabeth Fisher, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 355 days.

(21) Appl. No.: 15/642,998

(22) Filed: Jul. 6, 2017

(65) Prior Publication Data

US 2018/0012354 A1  Jan. 11, 2018

Related U.S. Application Data

(60) Provisional application No. 62/359,872, filed on Jul. 8, 2016.

(51) Int. Cl.
*G06T 7/00* (2017.01)
*G06T 7/62* (2017.01)
(Continued)

(52) U.S. Cl.
CPC .......... *G06T 7/0012* (2013.01); *A61B 5/0042* (2013.01); *A61B 5/055* (2013.01); *A61B 5/4064* (2013.01); *G06T 7/62* (2017.01); *G06T 2207/10088* (2013.01); *G06T 2207/30016* (2013.01)

(58) Field of Classification Search
None
See application file for complete search history.

(56) References Cited

U.S. PATENT DOCUMENTS

2012/0027271 A1 * 2/2012 Zankowski ............... G06T 7/11
382/128

FOREIGN PATENT DOCUMENTS

WO  WO 2002/101407 A2  12/2002
WO  WO-02101407 A2 * 12/2002 ............. G01R 33/56

OTHER PUBLICATIONS

Nakamura et al. (2009). Segmentation of Brain Magnetic Resonance Images for Measurement of Gray Matter Atrophy in Multiple Sclerosis Patients. Neuroimage. 44(3):769-776. doi:10.1016/j.neuroimage.2008.09.059 (Year: 2009).*

(Continued)

*Primary Examiner* — Angela M Hoffa
*Assistant Examiner* — Younhee Choi
(74) *Attorney, Agent, or Firm* — Bookoff McAndrews, PLLC

(57) ABSTRACT

A brain volume (BV) calculation method includes obtaining a first set of medical images at a first time point and a second set of medical images at a second time point, each set including at least two medical images. First and second algorithms may be used to calculate, respectively, first and third BV values at the first time point based on two or more images from the first set of medical images, and second and fourth BV values at the second time point based on two or more images from the second set of medical images. A mathematical weight may be applied to at least one of the first to fourth BV values. The first and third BV values may be averaged, and the second and fourth BV values may be averaged to determine overall BV values at the first and second time points, respectively.

23 Claims, 5 Drawing Sheets

(51) Int. Cl.
*A61B 5/00* (2006.01)
*A61B 5/055* (2006.01)

(56) References Cited

OTHER PUBLICATIONS

Landman et al. (2011). Multi-Parametric Neuroimaging Reproducibility: A 3T Resource Study. Neuroimage. 54(4): 2854-2866. doi:10.1016/j.neuroimage.2010.11.047 (Year: 2011).*

Wetzel et al. (2002). Three-Dimensional, T1-Weighted Gradient-Echo Imaging of the Brain with a Volumetric Interpolated Examination. AJNR AM J Neuroradiol. 23:995-1002 (Year: 2002).*

Everitt, B. (2006). The Cambridge Dictionary of Statistics (vol. 3rd ed). Cambridge, UK: Cambridge University Press. (Year: 2006).*

Deeley et al. (2011). Comparison of manual and automatic segmentation methods for brain structures in presence of space-occupying lesions: a multi-expert study. Phys Med Biol. 56(14): 4557-4577. doi:10.1088/0031-9155/56/14/021 (Year: 2011).*

International Search Report and Written Opinion cited in PCT/US2017/040913, dated Oct. 12, 2017 (17 pages).

Khanal, B. et al., Simulating Longitudinal Brain MRIs with Known Volume Changes and Realistic Variations in Image Intensity, *Frontiers in Neuroscience*, Mar. 22, 2017, pp. 1-18, vol. 11.

Nakamura, K. et al., Segmentation of brain magnetic resonance images for measurement of gray matter atrophy in multiple sclerosis patients, *NeuroImage*, Feb. 1, 2009, pp. 769-776, vol. 44(3), Elsevier, Amsterdam, NL.

Roy, S. et al., Longitudinal Intensity Normalization in the Presence of Multiple Sclerosis Lesions, *IEEE Int Symp Biomed Imaging*, Apr. 1, 2013, pp. 1384-1387.

Pluim, J. et al., Mutual information based registration of medical images: a survey, *IEEE Transactions on Medical Imaging*, 2003, pp. 1-21.

* cited by examiner

METHODS FOR IMPROVED MEASUREMENTS OF BRAIN VOLUME AND CHANGES IN BRAIN VOLUME

CROSS-REFERENCE TO RELATED APPLICATIONS

This application claims benefit of priority from U.S. Provisional Application No. 62/359,872, filed on Jul. 8, 2016, the entirety of which is incorporated by reference herein.

TECHNICAL FIELD

Embodiments of the present disclosure relate generally to methods of analyzing images—in particular, non-invasive medical images—using multiple algorithms. Specifically, embodiments of the present disclosure relate to methods for calculating brain volume and/or changes in brain volume using multiple algorithms to analyze multiple types of images acquired at a single time point or over two or more different time points.

BACKGROUND

Brain volume ("By") measurements from magnetic resonance images ("MRIs") are useful for monitoring changes in brain volume, as may be caused by neurological diseases, such as multiple sclerosis ("MS") and Alzheimer's disease. Many different techniques exist to measure BV, including, for example, manual analysis of MRIs, such as stereological or tracing methods, or by semi-automated or automated methods, using software algorithms. Various types of image analysis software programs have been developed recently to measure BV in research settings, and much of the software available for calculating BV has been generated by universities.

However, BV measurement software has been slow to translate to more general, clinical use within the wider healthcare system. This is in part because even with the most precise techniques available, day-to-day BV measurements for a patient may vary due to technical and/or biological factors. Technical factors that may corrupt BV measurements include, for example, patient movement during imaging, signal-to-noise ratio, image contrast-to-noise ratio, image artifacts, and algorithm performance. Biological factors include hydration status, inflammatory edema, changes in pressure caused by cerebrospinal fluid, brain injury, and diurnal fluid fluctuations, among others. Currently, there are no software algorithms available that are capable of differentiating between the effects of technical versus biological factors on BV measurements. Because software algorithms generally have been unable to accurately and reliably distinguish between actual biological fluctuations in BV and technical noise, such techniques have not been widely adopted to calculate BV measurements for patients in routine clinical care. As a result, these short-term fluctuations in BV have hindered the transition of algorithms to calculate BV from use as a research tool to use in clinical settings.

Accordingly, there exists a need for a method of calculating BV and/or change in BV that can be used to provide metrics for routine patient care. Specifically, there is a need for a method of calculating BV that is capable of distinguishing between fluctuations in BV measurements due to biological versus technical factors.

SUMMARY OF THE DISCLOSURE

Embodiments of the present disclosure are directed to methods of calculating brain volume of a patient. Methods of the disclosure may include obtaining a first set of medical images at a first time point and a second set of medical images at a second time point, each set including at least two medical images. First and second algorithms may be used to calculate, respectively, first and third brain volume (BV) values at the first time point based on two or more images from the first set of medical images and second and fourth BV values at the second time point based on two or more images from the second set of medical images. A mathematical weight may be applied to at least one of the first, second, third, or fourth BV values. The first and third BV values may be averaged, and the second and fourth BV values may be averaged to determine overall BV values at the first and second time points, respectively.

Various embodiments of the disclosure may include one or more of the following aspects: the medical images may be magnetic resonance images; the first algorithm may use MPRAGE-based magnetic resonance images from the first set of images and the second set of images to calculate the first brain volume and the second brain volume, respectively; the second algorithm may use FLAIR-based magnetic resonance images from the first set of images and the second set of images to calculate the third brain volume and the fourth brain volume, respectively; the method may further comprise obtaining a third set of medical images of the patient's brain at a third time point, wherein the third set of medical images includes at least two medical images; the method may further comprise obtaining an image quality score for each of the medical images from the first set of medical images and for each of the medical images from the second set of medical images; the mathematical weight may be applied based on an image quality score obtained for at least one of the medical images from the first set of medical images or the second set of medical images; the method may further comprise calibrating the first, second, third, and fourth brain volume values using a predetermined calibration equation; the predetermined calibration equation may be an equation for calculating a best-fit regression line; the method may further comprise plotting the first, second, third, and fourth brain volume values on a graph; the first, second, third, and fourth brain volume values may be brain volume measurements; and the first, second, third, and fourth brain volume values may be brain volume change measurements.

Embodiments of the present disclosure are also directed to methods of calculating a volume of an organ in a patient. Exemplary methods may include obtaining a first plurality of magnetic resonance images of the organ from a first time point, and obtaining a second plurality of magnetic resonance images of the organ from a second time point, different than the first time point. The methods may also include using a first algorithm to calculate the volume of the organ at the first time point based on at least one of the first plurality of magnetic resonance images, and using the first algorithm to calculate the volume of the organ at the second time point based on at least one of the second plurality of magnetic resonance images. The methods may further include using a second algorithm, different than the first algorithm, to calculate the volume of the organ at the first time point based on at least one of the first plurality of magnetic resonance images, and using the second algorithm to calculate the volume of the organ at the second time point based on at least one of the second plurality of magnetic resonance images. The methods may then include applying a mathematical weight to at least one of the volumes calculated at the first time point and the second time point. After applying the mathematical weight, the method may include averaging the volume of the organ calculated by the first algorithm and the volume of the organ calculated by the second algorithm at the first time point, and averaging the volume of the organ calculated by the first algorithm and the volume of the organ calculated by the second algorithm at the second time point.

Various embodiments of the disclosure may include one or more of the following aspects: the first plurality of magnetic resonance images and the second plurality of magnetic resonance images may include MPRAGE-based magnetic resonance images and FLAIR-based magnetic resonance images; the first algorithm may be used to calculate the volume of the organ at the first time point and at the second time point based on the MPRAGE-based magnetic resonance images; the second algorithm may be used to calculate the volume of the organ at the first time point and at the second time point based on the FLAIR-based magnetic resonance images; the method may further comprise calculating a change in organ volume based on the averaged volume at the first time point and the averaged volume at the second time point; and the method may further comprise using a third algorithm to calculate the volume of the organ at the first time point based on at least one of the first plurality of magnetic resonance images, and using the third algorithm to calculate the volume of the organ at the second time point based on at least one of the second plurality of magnetic resonance images, wherein averaging the volume of the organ at the first time point includes averaging the volume of the organ calculated by the first algorithm, the second algorithm, and the third algorithm at the first time point, and averaging the volume of the organ at the second time point includes averaging the volume of the organ calculated by the first algorithm, the second algorithm, and the third algorithm at the second time point.

Additional embodiments of the present disclosure are directed to methods of calculating a volume of an organ in a patient. The methods may comprise obtaining at least one MPRAGE-based magnetic resonance image of the organ from each of a first time point and a second time point, and obtaining at least one FLAIR-based magnetic resonance image of the organ from each of the first time point and the second time point. The methods may also include using a first algorithm to calculate the volume of the organ at the first time point based the at least one MPRAGE-based magnetic resonance image from the first time point, and using the first algorithm to calculate the volume of the organ at the second time point based the at least one MPRAGE-based magnetic resonance image from the second time point. The methods may further include using a second algorithm to calculate the volume of the organ at the first time point based the at least one FLAIR-based magnetic resonance image from the first time point, and using the second algorithm to calculate the volume of the organ at the second time point based the at least one FLAIR-based magnetic resonance image from the second time point. Steps of the methods may include averaging the volume of the organ calculated by the first algorithm and the volume of the organ calculated by the second algorithm at the first time point, and averaging the volume of the organ calculated by the first algorithm and the volume of the organ calculated by the second algorithm at the second time point.

Various embodiments of the disclosure may include a method further comprising calculating a change in organ volume based on the averaged volume at the first time point and the averaged volume at the second time point.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. In the drawings.

DETAILED DESCRIPTION

Figure 1:
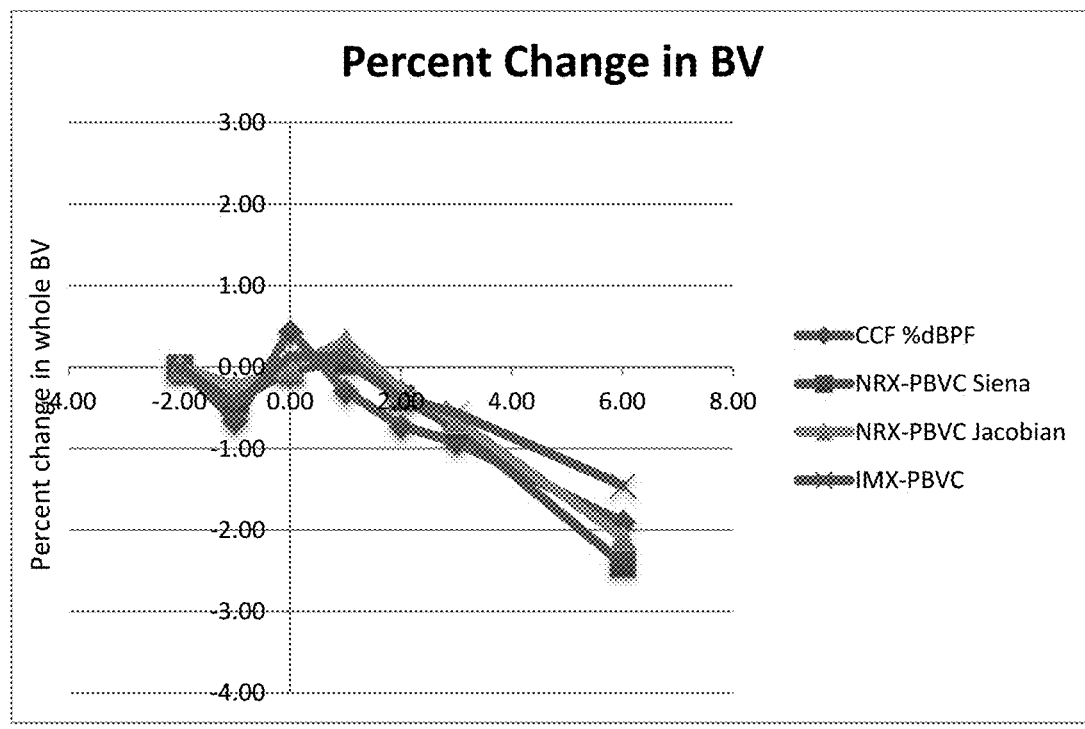
FIG. 1 shows the percent change in BV calculated using four different algorithms, according to an embodiment of the present disclosure.

Reference will now be made in detail to the exemplary embodiments of the present disclosure described below and illustrated in the accompanying drawings. Wherever possible, the same reference numbers will be used throughout the drawings to refer to same or like parts. The term "exemplary" is used herein to mean "example," rather than "ideal." The terms "algorithm" and "technique" are used synonymously. The term "subset" as used herein refers to one or more than one element that is contained within a "set." For example, a subset of images may refer to one image or multiple images contained within a set of images. Additionally, "BV change" may refer to either decreases or increases in BV. Further, BV values may be calculated for the whole brain, or may be calculated for specific regions of the brain.

Although embodiments of the disclosure are drawn to measuring brain volume and measuring changes in brain volume, the method described herein may be used to assess the volume of any suitable body tissue or organ. Further, embodiments of the disclosure may also be used to measure other characteristics of body tissues other than volume, for example, density, perfusion, fluid flow, fluid pressure, or other suitable characteristics. Biological parameters other than brain volume may alternatively be assessed, including, e.g., glucose value, bone density, plaque build up, or tissue perfusion.

Over time, monitoring of BV may help to monitor disease progression, treatment success, etc. Generally, patients with diseases that cause a loss in BV should be monitored over time to assess BV measurements at a given time point, the change in BV compared to a prior BV calculation at a prior time point, and/or the rate of change in BV over time. For example, MS patients typically undergo MRI examinations regularly as part of their care in order to assess and monitor disease progression and efficacy of treatments. A given MS patient may undergo, for example, multiple MRI scans over the course of a year. During each MRI scan, multiple types of MRIs may be acquired at that one point in time, typically including, for example, T2-weighted fluid-attenuated inversion recover (FLAIR), T1-weighted three-dimensional magnetization-prepared gradient echo (MPRAGE), T1-, T2-, or proton density-weighted spin echo images. These images are typically assessed visually by a radiologist to qualitatively assess changes over time. Alternatively, if the technology is available, the MRIs acquired at a given point in time may be analyzed to quantitatively measure BV. BV measurements at different time points may be compared, and, ultimately, brain volume changes may be assessed for the patient over time.

The inventor conducted a head-to-head comparison of the technical performance of six different BV measurement algorithms. MRIs were previously acquired from a set of MS patients. Each MS patient was imaged monthly for a period of six months, and a final set of MRIs was taken three months later, for a total of seven MRI time points per patient. For each patient, the MRIs from each time point were analyzed using multiple algorithms. Each algorithm used one or more of the MRIs at a given time point to calculate BV or change in BV. That is, some algorithms used the MPRAGE image as input, while others used the FLAIR image as input to calculate BV, for example.

The BV measurement results generated by each algorithm were then assessed. For each algorithm and each individual patient, a best-fit regression line was calculated based on the BV results. Time was plotted along the x-axis, and the percent change in BV relative to the initial BV measurement was plotted along the y-axis. Each data point on the scatter plots generated represented the BV percent change measurement calculated by the algorithm based on the MRIs acquired at a given point in time. The regression line calculated for each scatter plot represented the average rate of BV change based on the individual data points. Short-term fluctuations in BV were evident in addition to stable or slowly decreasing BV for each patient over time.

Measurement error for each algorithm was then estimated for each algorithm. In the study, measurement error was defined as the mean of the residuals, i.e., the average of the absolute distances from each BV measurement at a given time point to the best-fit BV regression line calculated for an individual patient. Four of the six BV algorithms performed similarly to each other, with similarly low residuals, while two of the algorithms had high residuals, and thus high measurement errors. Thus, the BV calculation for MRIs of an individual patient at a given point in time could be assessed relative to the overall trend in BV change for that patient, and the reproducibility of the algorithm could be assessed based on the fluctuations around the trend lines. For each patient, the percent BV measurement change results for the four BV algorithms that performed similar to each other (brain parenchymal fraction (BPF), SIENA, and two instantiations of Jacobian integration) were then plotted on the same graph, as shown in FIG. 1.

Initially, the expectation was that algorithms that performed similarly well would show similar lines of BV regression, but that the short-term fluctuations in percent change in BV at each time point for each algorithm would be random. In other words, the expectation was that the fluctuations in BV change for each algorithm at a given time point would be due to measurement error, and thus, the errors for each algorithm would be different. Unexpectedly, however, it was found that the short-term fluctuations around the regression lines for the different algorithms were generally synchronous, as depicted in FIG. 1.

In many cases, the fluctuations were highly similar across the different algorithms. This was even more unexpected because the algorithms used different input image types (MPRAGE, FLAIR, or the combination) to calculate BV. The MPRAGE-based algorithms could be expected to demonstrate synchronous fluctuations if each of the algorithms was fairly precise, because when the input images are the same, technical factors, such as patient motion, should affect all of the BV measurements for all of the algorithms similarly. Yet, it was found that the FLAIR-based algorithm was often synchronized with the other MPRAGE-based algorithms. There were some instances, however, in which the fluctuations noticeably diverged across algorithms with different input images.

As a result of these unexpected observations, it was deduced that if the technical factors differ due to different input images, but the fluctuations are highly similar across algorithms, then there is an increased likelihood that the factors driving the synchronous fluctuations are biological factors, while the factors driving the asynchronous fluctuations are technical factors.

Based on this surprising study observation, a new approach for measuring BV in individual patients was invented. As described above, in prior studies of BV change, a single algorithm was chosen to assess BV and BV change. Studies performed previously had generally focused on determining the accuracy of each algorithm to identify the algorithm best suited for a particular use. Indeed, the original study described herein initially set out to do the same. By contrast, in at least certain embodiments, the new method invented based on the surprising results uses at least two different algorithms applied to different input image types independently to calculate BV from each time point, and then combines the BV calculations of each algorithm to estimate BV or change in BV at that time point, as described below in the various embodiments. Accordingly, the new method may differentiate between technical versus biological effects. And, as a result, the new method may reduce the influence of undesirable technical effects on BV calculations and more-reliably calculate change in BV, thus promoting use of such algorithms in clinical medicine.

Embodiments of the disclosed method take advantage of combined analyses and use multiple independent algorithms that operate on two or more MRIs (or other types of medical images) taken at a particular time point to estimate change in BV across time points, while reducing influence from technical factors. First, multiple MRIs (or other medical image types) of a patient's brain may be acquired at one or more time points. In some embodiments, one time point may be used to estimate BV, two time points may be used to calculate BV change or BV at each time point, or multiple time points may be used. The patient may have—or be suspected of having—a disease associated with brain volume change (either BV decrease or increase), for example, MS, Alzheimer's, cerebral palsy, Pick's disease, Huntington's disease, stroke, traumatic brain injury, fever, dementia, tumors, substance use, infection, hypertension, or other diseases. In some instances, MRIs of geriatric patients may be taken to assess potential age-related BV loss.

In some embodiments, once the MRIs are acquired, an image quality score may be determined for each MRI. Factors that make up an image quality score may include, e.g., quantitative measurements of patient motion artifacts, signal-to-noise ratio, image contrast-to-noise ratio, or combinations thereof. The image quality scores may be calculated automatically by the MRI scanner and output with the MRIs, or the scores may be calculated separately after the MRIs are generated, as is known in the art. Further, image quality scores may be calculated after each set of MRIs is acquired at each time point, or after all of the MRIs from the two or more time points have been acquired and prior to analysis by the various algorithms, or a combination thereof.

Two or more MRIs from each time point may be selected, and pluralities of MRIs from multiple different time points may be used to calculate BV at each time point using two or more different algorithms. The amount of time between each time point may be substantially constant (e.g., one set of MRIs per month may be analyzed) or may vary (e.g., one set of images taken once every 1-3 months, or once a month for the first several months and then over longer follow-up periods). The time points may be selected based on, for example, the unique level of monitoring required by an individual patient, disease progression or prognosis, correlations with clinical observations, treatment standards for a given disease, insurance reimbursement, or other suitable factors or combinations of factors.

Two or more algorithms may then be utilized to analyze the MRIs from each time point to calculate a BV measurement for each time point. In one embodiment, one or more MPRAGE-based algorithms may be used to calculate BV based on MPRAGE image input, and one or more different algorithms may be used to calculate BV change based on FLAIR image input. In such embodiments, the MRIs selected for assessment by the MPRAGE-based algorithms may be different than the MRIs selected for assessment by the FLAIR-based algorithms. For example, T1-weighted MRIs may be used for the MPRAGE-based assessment, and FLAIR MRIs may be used for the FLAIR-based assessment. In other embodiments, multiple MPRAGE-based algorithms may be selected, or multiple FLAIR-based algorithms may be selected, and the MRIs used for analysis by the different algorithms may be the same. For example, all T1-weighted images may be used or all FLAIR images may be used. It is also contemplated that other algorithms requiring other types of MRIs (or imaging techniques other than MRI) may be used instead of, or in combination with, one or more MPRAGE-based or FLAIR-based algorithms.

Figure 2:
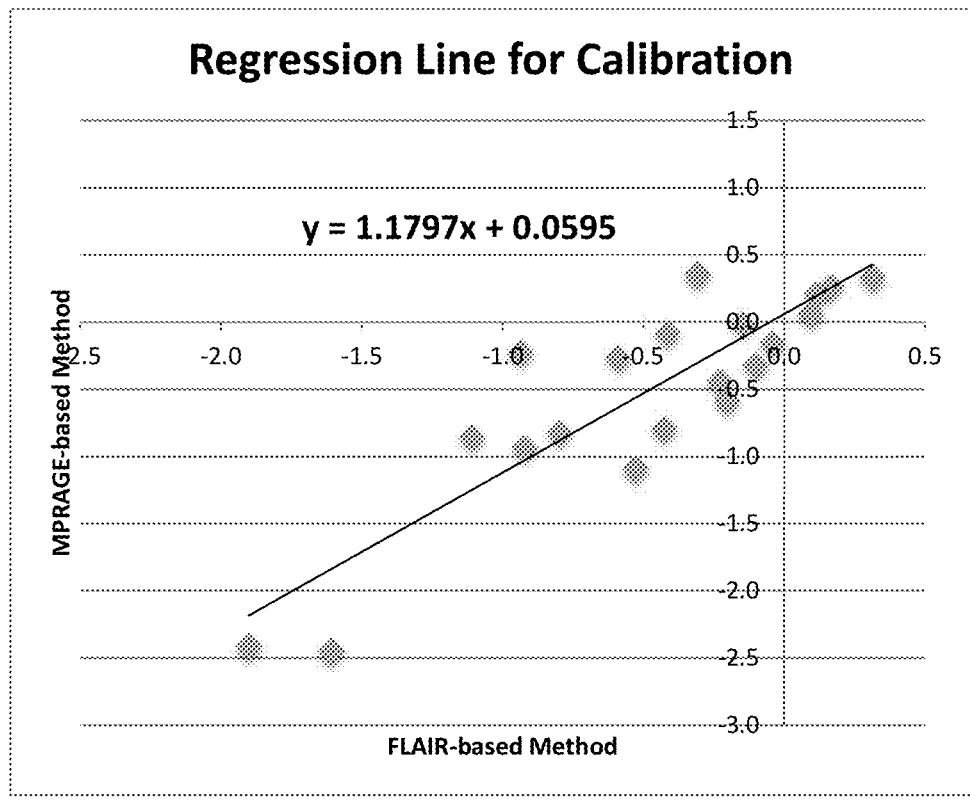
FIG. 2 is an exemplary scatter plot showing the percent BV change results obtained using two different algorithms and an exemplary best-fit regression line.

In some embodiments, if both MPRAGE-based and FLAIR-based algorithms are used, then an additional calibration step may be performed in order to calibrate the BV values or BV change values output by the different algorithms. For example, the BV values calculated by one algorithm may generally be higher or lower that the BV values calculated by the other algorithm. For example, FIG. 2 depicts an exemplary scatter plot showing the percent BV change results obtained using an MPRAGE-based algorithm versus those results obtained using a FLAIR-based algorithm. A best-fit line of regression was then calculated based on the results from the two different algorithms. In some embodiments, the equation of the best-fit line may then be used to convert the BV measurements obtained using a MPRAGE-based algorithm to the those obtained using a FLAIR-based algorithm, or vice versa, prior to combining the measurements generated by the two algorithms using a weighted average, as will be discussed in further detail below. While the best-fit line calculated for the exemplary data depicted in FIG. 2 was y=1.1797x+0.0595 (based on the equation y=mx+b), it is understood that the best-fit line calculation for any specific data set will depend on the BV dated generated for the algorithms and patient MRIs used.

In other embodiments, no calibration step may be performed.

As discussed above, there may be some advantages to using two different algorithms that operate on two different types of images (or, more generally, multiple algorithms with multiple types of image inputs). For example, because MPRAGE-based algorithms use different input images than FLAIR-based algorithms, synchronous fluctuations in BV should not be the result of shared image errors, because different images were used for each algorithm. By contrast, when the input image types are the same, technical factors, such as patient motion, should affect all of the BV measurements similarly. If different input images are used, then these technical factors would not uniformly affect the BV measurements across algorithms, because the algorithms would utilize different images. Thus, it would be more likely that synchronous fluctuations were correlated with biologic changes rather than technical errors in the MRIs used. Stated another way, using algorithms that require different input images may increase the likelihood that fluctuations in BV measurements reflect biological variations in BV, instead of technical error.

In some embodiments, errors in MRIs may be controlled for by using separate sets of MRI inputs for two algorithms of the same 'type' instead of, or in addition to, using algorithms that use different input types (e.g., MPRAGE and FLAIR based). For example, even if more than one MPRAGE-based algorithm or more than one FLAIR-based algorithm is used, different MRIs from the same time point may be used as input for the different algorithms. Thus, if four MRIs of the same type are taken at each time point, two images may be used to calculate BV using a first MPRAGE (or FLAIR-based) algorithm, and two different images may be used to calculate BV using a second MPRAGE (or FLAIR-based) algorithm. In this way, errors in imaging may be controlled for even if two or more algorithms using the same type of MRI input are used. An individual time point may span, for example, the time needed to take multiple MRIs during an individual patient visit. The images taken at a single time point should be temporally close to one another.

The algorithms used in exemplary methods of the disclosure may include one or more of, e.g., BPF, SIENA, or Jacobian integration, as described in the initial study. Other available BV measurement algorithms may also be chosen in addition to, or instead of, the algorithms listed above. In some embodiments, the set of algorithms may be selected as part of the method, or, in some embodiments, the set of algorithms may be pre-determined, and this step may not be included in the overall method.

Once the set of two or more algorithms has been chosen or has been pre-determined, the MRIs from each time point may be analyzed using each of the selected algorithms, and BV measurements may be calculated using each algorithm for each time point based on the MRIs from the respective time points, using the appropriate different types of MRIs as required input for each algorithm. Or, even if the same type of MRI input is required for the different algorithm, different MRIs from the same time point may be used for each algorithm in order to help control for any technical error in each set of MRI images.

For each time point, the change in BV may be calculated. The change in BV at each time point may be calculated relative to the first, initial time point. In some embodiments, the change in BV at the various time points may be calculated relative to a preceding time point other than the first time point, e.g., the immediately preceding time point (except, this this case, the second time point would use the immediately preceding first time point to calculate change). Either the BV measurement or the BV change calculated at each time point using each algorithm may be plotted for comparison. In some embodiments, the change in BV may be calculated as a percentage, and the percent change in BV may be plotted. As used herein, the term "BV value" refers generally to the BV measurement, the change in BV at that time point compared to a preceding time point, or the percent change in BV.

The independently derived BV values generated by the various algorithms applied to various images may be assessed relative to one another. The time points are the same across the various algorithms, so the BV measurements or BV change measurements calculated by each algorithm at each time point may be compared with one another to determine whether fluctuations in BV or in BV change between algorithms across the time points are synchronous or asynchronous. If the fluctuations in BV or in BV change between algorithms are synchronous, then the fluctuations may be more likely to be caused by underlying biological fluctuations that were detected by each of the algorithms, as opposed to technical errors. Accordingly, the final BV measurement at a given time point or the final BV change value may be an equally weighted average of the calibrated, independent measurements generated by each algorithm. In some embodiments, the synchronous BV measurements or percentage BV change generated by each algorithm may be weighted substantially equally, with slight weighting applied to one or more algorithms depending, e.g., on their image quality scores.

If fluctuations in BV measurements or percent change in BV are determined to be asynchronous, then each result may be further analyzed. For example, a reliability index may be calculated for each algorithm based on prior BV values and image quality metrics from the input images. The BV measurements or BV change measurements for each algorithm may be weighted according to the reliability indices calculated. In this way, the final BV or BV change measurement may be calculated as a reliability-weighted average of measurement results from different algorithms and different images, and the measurement results with lower reliability will contribute less to the final measurement than the measurement results with higher reliability. The weighted results may be combined to calculate BV or BV change at a given time point. As a result, the final measurement generated using this new method may be less significantly affected by technical noise.

If a subset of BV value fluctuations are synchronous, but another subset of fluctuations are not synchronous, then the asynchronous algorithms may be attributed less weight, or, in some embodiments, may be attributed a weight of zero, effectively removing the algorithms from the overall BV calculation. For example, in some embodiments, if fluctuations in BV measurements or percent change in BV for a particular algorithm or subset of algorithms varies too greatly from the other algorithm(s), then the results from that algorithm or those algorithms may be weighted less or removed from further analysis.

The BV values derived from each algorithm may be then weighted according to their individual reliability indices, measurement errors, or according to their degree of similarity with each other or with the other subset. Further, if one or more algorithms has a measurement error or reliability index that falls outside of a certain cutoff threshold, that algorithm may be accorded less weight or may be accorded no weight and may be removed from the final BV calculation.

In some embodiments, image quality scores may be used to calculate the reliability index and/or to calculate a weight to assign a particular algorithm or subset of algorithms (e.g., all FLAIR or all MPRAGE algorithms). For example, if the FLAIR image at a particular time point had a lower image quality score than that of an MPRAGE image at that time point, then some or all of the asynchrony at that time point may be due to the poorer image quality. Accordingly, that particular BV value at that time point for that algorithm may be weighted lower. Such weighting may reduce the effect of technical noise.

In some embodiments, weights for each algorithm may be based on a number of different factors in addition to, or instead of, input image quality. For example, weights may be calculated based on a combination of image quality score, historical data (e.g., historical reliability of an algorithm), measurement error (e.g., if measurement error for an algorithm falls within certain threshold parameters), how synchronous algorithms are with one another (e.g., if an algorithm results in BV values that are very similar with those of one or more other algorithms, then those algorithms with similar fluctuations may be weighted more heavily, or vice versa), or algorithm performance. In some embodiments, once different weights are calculated based on one or more different factors, the weights may be combined and applied to the results of the particular algorithm(s), and a single, combined BV measurement or BV change measurement may be calculated for the time points.

Figure 3A:
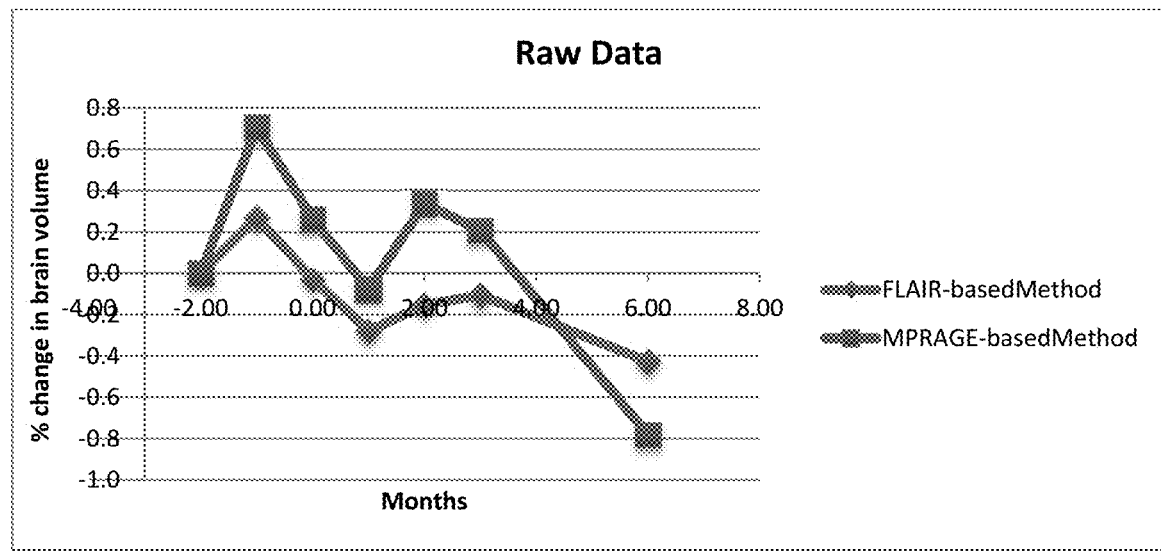
FIG. 3A graphically depicts raw BV measurements obtained over time using two different algorithms, each of which utilizes a different MRI type as input, according to a step of an exemplary method of the disclosure.
Figure 3B:
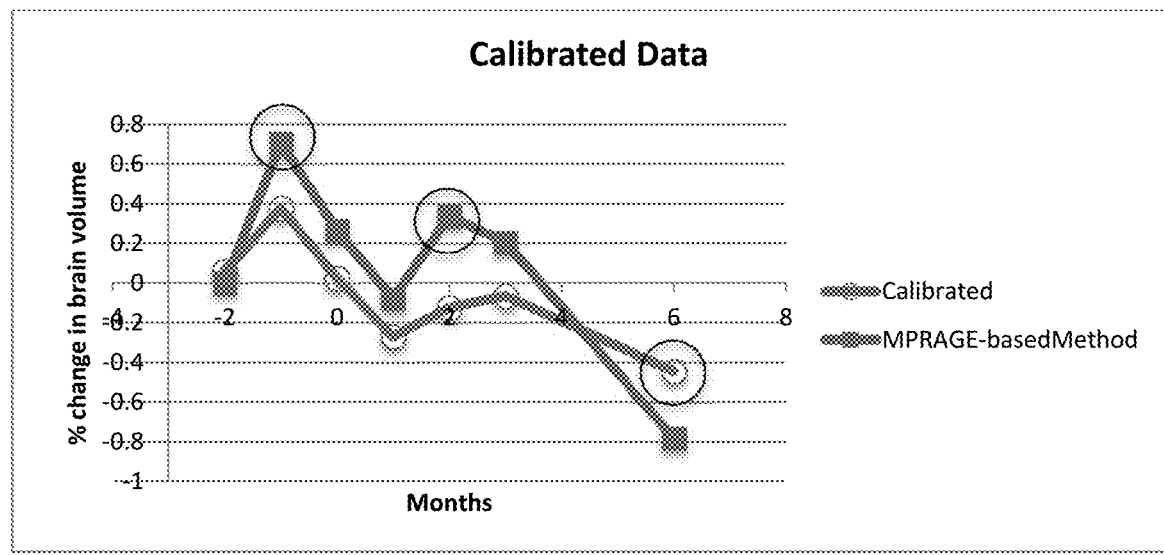
FIG. 3B graphically depicts the BV measurements of FIG. 3A after calibration between algorithms, according to a step of an exemplary method of the disclosure.
Figure 3C:
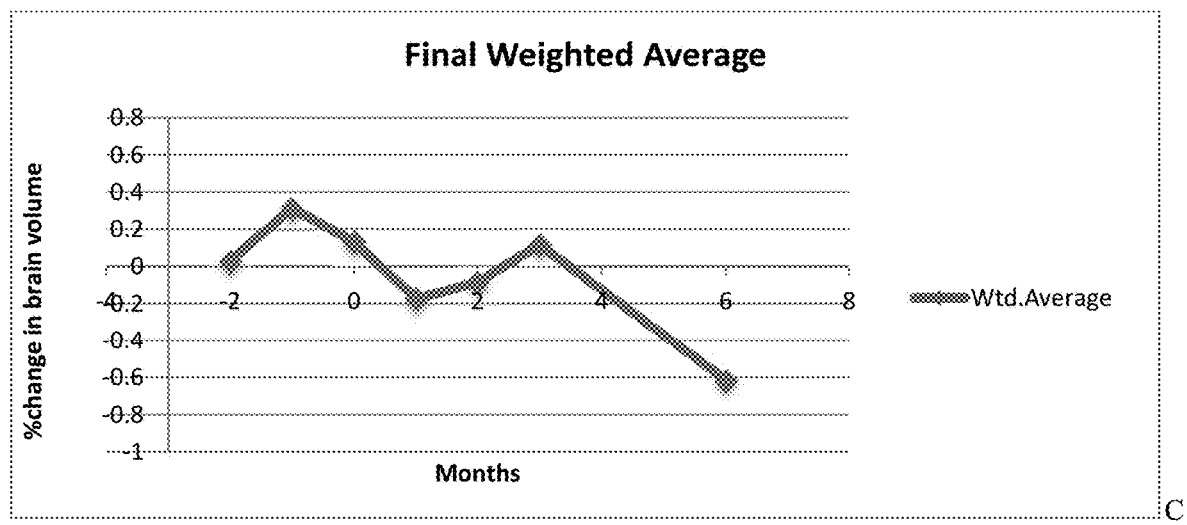
FIG. 3C graphically depicts the weighted average of BV measurement results of the two algorithms used in FIGS. 3A and 3B, according to a step of an exemplary method of the disclosure.

FIGS. 3A-3B graphically depict BV change results generated at various steps of an exemplary method of the disclosure. As described above, the exemplary method of FIGS. 3A-3B utilizes multiple algorithms applied to multiple images to measure BV change. In this embodiment, image quality scores were initially measured for each MRI used to calculate BV change. FIG. 3A graphically depicts exemplary raw data obtained using two different algorithms for measuring BV change. The two algorithms depicted in FIG. 3A utilized as input two different MRI types (e.g., FLAIR and MPRAGE) acquired at each time point. FIG. 3B graphically depicts the BV data generated by the two algorithms in FIG. 3A after calibrating the data. As described above, calibration between algorithms may be performed in a number of different ways. In the example of FIG. 3B, a best-fit line of regression was calculated based on the results from the two different algorithms, and the best-fit regression line was used to calibrate the FLAIR-based algorithm with the MPRAGE algorithm, as described in reference to FIG. 2. Data points for which MRIs with lower image quality scores were used to calculate BV at a given time point are indicated with circles. The data generated by each algorithm was then weighted based on the image quality scores, and the weighted results for the two algorithms were then averaged together. FIG. 3C graphically depicts the final BV measurement results obtained by calculating the weighted average of both algorithms. In the embodiment of FIG. 3C, the weights are determined from image quality scores as follows:

weight_1=qualityscore_1/(qualityscore_1+qualityscore_2), adj_weight_i=weight_i and if weight_i<weight_j, weight_i<0.5 then adj_weight_i=0. Final Result=adj_weight_1*result_1+adj_weight_2*result_2.

In some embodiments, a confidence calculation, confidence range, and/or standard deviation may be calculated for each algorithm. These factors may then affect the weighting ascribed to each data point or to algorithm results overall. Or, these factors may be calculated separately and used to assess each algorithm before and/or after weighting is applied. In some embodiments, the final BV calculation or BV change calculation arrived at after combining the results of the algorithms may include a confidence score or confidence range or may be output with a standard deviation value, for example.

In some embodiments, calibration between different algorithms may be conducted prior to, during, or after the weighting process. For example, a single MRI may be analyzed by each technique, and, based on the algorithm output, a calibration factor may be determined. In some embodiments, that calibration factor may also be determined at least in part based on clinical observation or independent analysis of the MRI by a clinician. The calibration factor may then be applied to the algorithms either before, during, or after the weighting process.

In some embodiments, a new set of images from current/recent time points may be analyzed and compared to BV calculations made based on images from an older set of time points analyzed previously to measure BV and/or BV change. For example, a patient with MS may have been monitored previously for changes in BV using a single algorithm, in accordance with the prior art. As a result, BV change data may already exist for the patient based on image analysis from the set of older time points. If the same patient is now monitored using one of the new methods for calculating BV change described herein, then the new BV change calculations generated from the new method based on images from the new time points may be compared to the set of older BV calculations made previously using one of the known, prior art algorithms. Because the new methods described herein may be capable of distinguishing between physiological and technical fluctuations, they may be more accurate than the BV change data collected previously for that patient before the new techniques described herein were available. Accordingly, the newer calculations based on images from current/more recent time points may show variations in BV change between the older and newer calculations that reflect the increased accuracy of the new method rather than an actual change in the rate of BV decrease or increase.

In such embodiments, the algorithms used in the new methods may be weighted differently to reflect the past measurements taken. For example, the BV change measurements at the past time points may affect the weighting of those algorithms used in the new method that generate BV measurements that fall closer to or further from the past BV change trends (e.g., regression line) measured previously. For example, in some embodiments, a preliminary step may be performed in which a line of regression for the set of older BV measurements may be calculated based on the old results. The old regression line may then be applied to the new BV change measurements generated from the set of algorithm techniques used according to the new method to calculate measurement error for the new results. The measurement error for the new results may then be used to weight the new results so that the new results may be calibrated to fall in line with the old BV measurements. In some embodiments, if the original single algorithm used to calculate the old BV measurements may be selected as one of the algorithms chosen for use in combination with one or more other algorithms to perform the new method, and then that original algorithm may be weighted more heavily to promote consistency between the old and new BV measurements. Such steps may help to reduce the effects of inconsistencies between old and new BV calculation methods, which, for example, may indicate a comparatively slower or faster rate of BV decline as a result of the improved accuracy of the new BV calculation method rather than as a result of an actual biological change in BV decline or increase in the patient.

While the original study described herein used six algorithms, of which four were ultimately selected for use in the final BV calculations, any suitable number of algorithms (e.g., two or more) may be used to perform embodiments of this method. As described above, algorithms may be selected based on different criteria. For example, each algorithm may be required to have a scan-rescan reproducibility falling within a predetermined threshold range in order to be included in the overall BV calculation. In some embodiments, more algorithms may be performed originally than are ultimately used to calculate final, overall BV values, and removal of certain algorithms may be due to, e.g., asynchrony with the other algorithms, measurement error falling outside of a certain threshold, or other factors or combinations of factors. In some embodiments, the number of algorithms performed may be the same as the number of algorithms ultimately used to calculate the final, overall BV values.

In some embodiments, a standard set of algorithms may consistently be used to measure BV, of which some may be removed based on BV measurement or BV change results, or all may be included in the final BV measurements, regardless of results. In the latter case, asynchrony may be dealt with by weighting, e.g., in order to compensate for potential error. In other embodiments, different sets of algorithms may be selected based on, e.g., availability, vendor backlog or turn-around time (if the MRIs are sent to vendors for algorithm assessment), disease type, disease progression, clinical symptoms, rate of BV change, frequency of MRIs, MRI type, MRI quality, the duration of the time period being assessed, insurance coverage, the location of the clinical practice, or other factors, or combinations of factors. For example, certain diseases, like MS, may require more-frequent detection of smaller changes in BV, and thus may require more precise algorithms to be used. Other diseases may require only detection of larger changes in BV (e.g., Parkinson's, Alzheimer's, or trauma). Some algorithms may be more suitable for measuring larger BV changes and/or BV change over longer time periods, and some algorithms may be more suitable for measuring smaller BV changes and/or changes over shorter time periods.

While the study described herein used two MRIs from each time point, it is contemplated that more than two MRIs from each time point could be used. In theory, the more images used, the more accurate the algorithms and the final BV calculation may be, because technical imaging error and image score would have a decreased effect. The number of images used ultimately may be limited due to practical constraints, e.g., the cost of acquiring and/or analyzing additional images, the health of the patient or ability of the patient to remain still, or other factors. Additionally, there may be a point of diminishing returns.

Additionally, while T1-weighted and FLAIR image types are described herein, it is contemplated that other image types, e.g., T1-, T2-, or proton density-weighted spin echo images, may also be used. In general, the type of image used will be determined based on the input required by the algorithms used. Thus, any suitable type of image input may be used according to what is required by the selected algorithms used to calculate BV.

One exemplary embodiment may include selecting at least two algorithms to calculate BV based on at least two MRIs from each of at least two different time points. The results in BV measurements at each time point or the change in BV calculated at each time point relative to an initial scan or preceding scan may then be plotted on a graph. The BV results from each algorithm may then be compared relative to each other to determine whether the fluctuations in BV or BV change across time points are synchronous or asynchronous. The output from one subset of algorithm(s) or each algorithm may be weighted according to, e.g., image quality score of the input MRIs used for that algorithm, the degree of synchrony or asynchrony, measurement error, or other suitable factors or combination of factors, as described above. The results from the different algorithms may then be combined using a weighted average, and a final overall BV measurement or BV change measurement may be generated.

Figure 4:
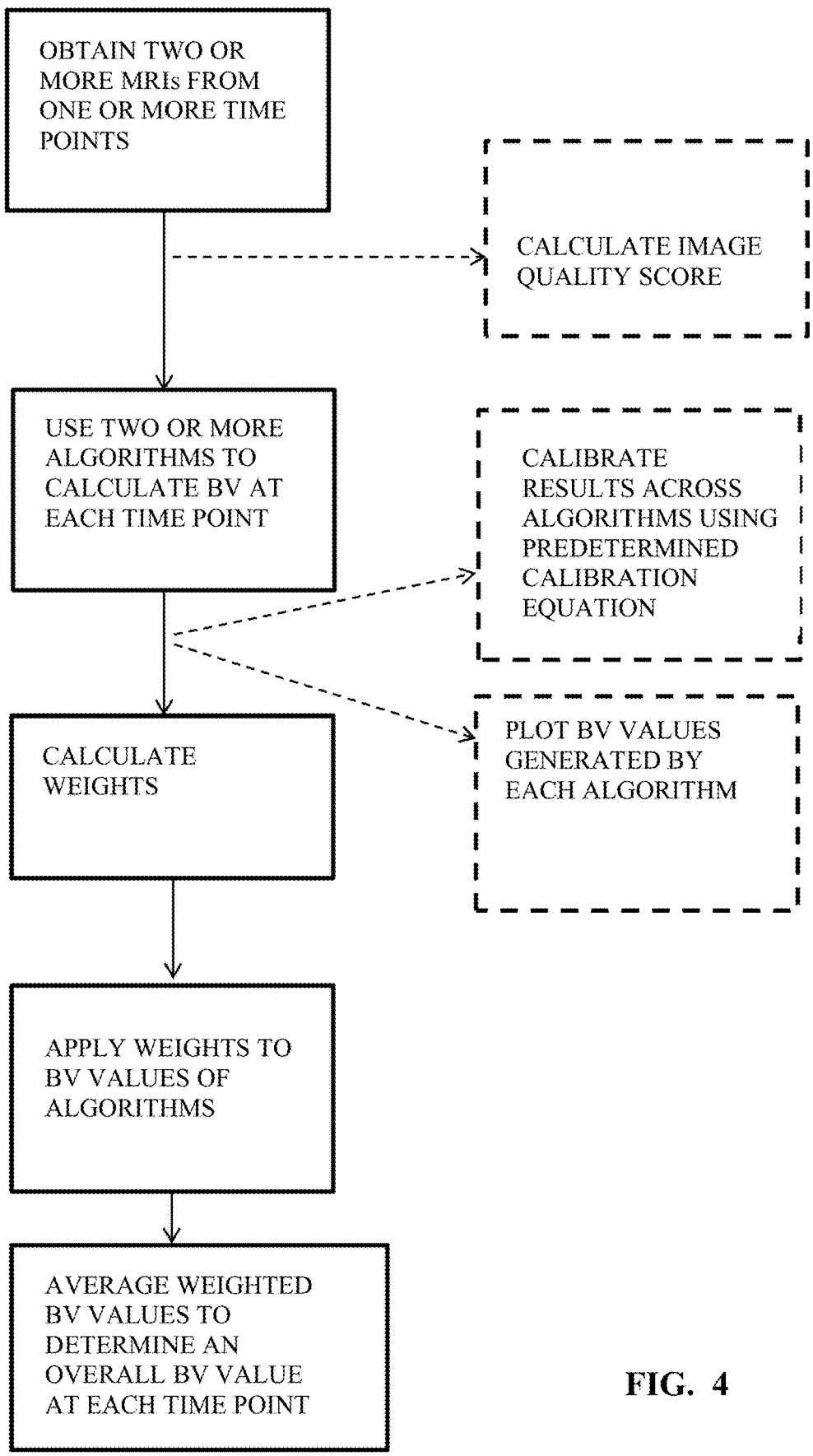
FIG. 4 is a flow chart illustrating an exemplary method for calculating BV and/or changes in BV, including optional steps, according to exemplary embodiments of the disclosure.

FIG. 4 is a flow chart depicting steps for calculating BV measurements or changes in BV according to exemplary embodiments of the present disclosure. FIG. 4 includes optional steps (shown in broken lines) that may or may not be included in the method, as described below in further detail. Note, however, that in some embodiments, one or more steps shown in solid lines may or may not be omitted.

As shown in FIG. 4, two or more MRIs may be obtained from one or more time points. The method may optionally include calculating image quality scores for each of the MRIs obtained. Next, two or more algorithms may be used to calculate BV at each time point based on the MRIs obtained from that time point. BV values generated using different algorithms may optionally be calibrated using a predetermined calibration equation (e.g., y=mx+b to calculate a best-fit line of regression). If measurements from multiple time points are available, calibrated BV values generated by each algorithm at each time point may then be plotted on a graph, with time plotted along the x-axis and the BV values plotted along the y-axis. The plotted BV values may be in the form of raw BV measurements, BV change (e.g., at that particular time point compared to a prior time point), or percent BV change. The method may then include comparing the fluctuations in BV values for each algorithm to assess synchrony or asynchrony.

Weights may then be applied to the BV values of each algorithm. The weights may be applied based on one or more of, e.g., image quality score, historical data (e.g., historical reliability of an algorithm), measurement error (e.g., if measurement error for an algorithm falls within certain threshold parameters), how synchronous algorithms are with one another (e.g., if an algorithm generates BV values that are very similar with those generated by one or more other algorithms, then those algorithms with similar results may be weighted more heavily, or vice versa), or algorithm performance. Weights may be applied equally to the BV values generated from each algorithm or may not be applied equally to the BV values generated from each algorithm. Further, within a given algorithm, weights may or may not be applied equally to each BV value generated at each time point using that algorithm. The BV values (including weights, if applied) at each time point for each algorithm may then be averaged together to determine an overall final BV value at each time point.

The many features and advantages of the present disclosure are apparent from the detailed specification, and thus, it is intended by the appended claims to cover all such features and advantages of the present disclosure that fall within the true spirit and scope of the disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A method of calculating a brain volume of a brain of a patient, the method comprising:
    obtaining a first plurality of magnetic resonance images (MRIs) of the brain at a first time point, wherein the first plurality of MRIs includes at least two first time point MRIs;
    obtaining a second plurality of MRIs of the brain at a second time point, wherein the second plurality of MRIs includes at least two second time point MRIs;
    calculating, with a first algorithm, a first brain volume value at the first time point based on the at least two first time point MRIs, and a second brain volume value at the second time point based on the at least two second time point MRIs;
    calculating, with a second algorithm, a third brain volume value at the first time point based on the at least two first time point MRIs, and a fourth brain volume value at the second time point based on the at least two second time point MRIs, wherein the second algorithm is different from the first algorithm;
    applying at least one of (a) a first algorithm mathematical weight to at least one of the first brain volume value and the second brain volume value, the first algorithm mathematical weight being associated with the first algorithm, to obtain a first mathematically-weighted value, and (b) a second algorithm mathematical weight to at least one of the third brain volume value and the fourth brain volume value, the second algorithm mathematical weight being associated with the second algorithm, to obtain a second mathematically-weighted value, wherein the first mathematically-weighted value is a product of the first algorithm mathematical weight and the at least one of the first brain volume value and the second brain volume value, and the second mathematically-weighted value is a product of the second algorithm mathematical weight and the at least one of the third brain volume value and the fourth brain volume value,
    wherein each of the first algorithm mathematical weight and the second algorithm mathematical weight is calculated based on at least one of: an image quality score, a reliability index of the corresponding algorithm, historical data of the corresponding algorithm, a measurement error of the corresponding algorithm, a synchronicity of the corresponding algorithm, a performance of the corresponding algorithm, and a degree of similarity with one or more other brain volume values; and determining an overall first time point brain volume value at the first time point by averaging the first brain volume value and the second mathematically-weighted value or by averaging the first mathematically-weighted value and the third brain volume; and determining an overall second time point brain volume value at the second time point by averaging the second brain volume value and the second mathematically-weighted value or by averaging the first mathematically-weighted value and the fourth brain volume value.

2. The method of claim 1, wherein each of the first plurality of MRIs and the second plurality of MRIs includes magnetization-prepared rapid acquisition gradient echo (MPRAGE)-based magnetic resonance images, and the first algorithm uses the MPRAGE-based magnetic resonance images from the first plurality of MRIs to calculate the first brain volume value, and the MPRAGE-based magnetic resonance images from the second plurality of MRIs to calculate the second brain volume value.

3. The method of claim 2, wherein each of the first plurality of MRIs and the second plurality of MRIs includes fluid-attenuated inversion recover (FLAIR)-based MRIs, and the second algorithm uses the FLAIR-based MRIs from the first plurality of MRIs to calculate the third brain volume value, and the FLAIR-based MRIs from the second plurality of MRIs to calculate the fourth brain volume value.

4. The method of claim 1, further comprising obtaining a third plurality of MRIs of the brain at a third time point, wherein the third plurality of MRIs includes at least two third time point MRIs.

5. The method of claim 1, further comprising obtaining the image quality score for at least one of the at least two first time point MRIs and the at least two second time point MRIs.

6. The method of claim 5, wherein each of the first algorithm mathematical weight and the second algorithm mathematical weights is based on the image quality score obtained for at least one of the at least two first time point MRIs and the at least two second time point MRIs.

7. The method of claim 1, further comprising calibrating the first brain volume value, the second brain volume value, the third brain volume value, and the fourth brain volume value using a predetermined calibration equation, wherein the predetermined calibration equation is an equation for calculating a best-fit regression line.

8. The method of claim 1, further comprising plotting the first brain volume value, the second brain volume value, the third brain volume value, and the fourth brain volume value on a graph.

9. The method of claim 1, wherein the first brain volume value, the second brain volume value, the third brain volume value, and the fourth brain volume value are brain volume measurements.

10. The method of claim 1, further comprising calculating a brain volume change based on a difference between the overall first time point brain volume value and the overall second time point brain volume value.

11. The method of claim 1, wherein a difference between the first time point and the second time point is at least one month.

12. The method of claim 1, wherein each of the first brain volume value, the second brain volume value, the third brain volume value, and the fourth brain volume value is calculated as a volume of the whole brain of the patient.

13. The method of claim 1, further comprising determining the first algorithm mathematical weight and the second algorithm mathematical weight based on the image quality score of images associated with the first algorithm and the second algorithm, respectively.

14. A method of calculating a volume of an organ in a patient, the method comprising:

obtaining a first plurality of magnetic resonance images of the organ at a first time point;

obtaining a second plurality of magnetic resonance images of the organ at a second time point, wherein the second time point is different from the first time point;

calculating, using a first algorithm, a first algorithm-first time point volume of the organ at the first time point based on at least one of the first plurality of magnetic resonance images;

calculating, using the first algorithm, a first algorithm-second time point volume of the organ at the second time point based on at least one of the second plurality of magnetic resonance images;

calculating, using a second algorithm, a second algorithm-first time point volume of the organ at the first time point based on at least one of the first plurality of magnetic resonance images, wherein the second algorithm is different from the first algorithm;

calculating, using the second algorithm, a second algorithm-second time point volume of the organ at the second time point based on at least one of the second plurality of magnetic resonance images;

applying at least one of (a) a first algorithm mathematical weight to at least one of the first algorithm-first time point volume and the first algorithm-second time point volume, the first algorithm mathematical weight being associated with the first algorithm, to obtain a first mathematically-weighted volume, and (b) a second algorithm mathematical weight to at least one of the second algorithm-first time point volume and the second algorithm-second time point volume, the second algorithm mathematical weight being associated with the second algorithm, to obtain a second mathematically-weighted volume, wherein the first mathematically-weighted volume is a product of the first algorithm mathematical weight and the at least one of the first algorithm-first time point volume and the first algorithm-second time point volume, and the second mathematically-weighted volume is a product of the second algorithm mathematical weight and the at least one of the second algorithm-first time point volume and the second algorithm-second time point volume, wherein each of the first algorithm mathematical weight and the second algorithm mathematical weight is calculated based on at least one of: an image quality score, a reliability index of the corresponding algorithm, historical data of the corresponding algorithm, a measurement error of the corresponding algorithm, a synchronicity of the corresponding algorithm, a performance of corresponding algorithm, and a degree of similarity with one or more other brain volume values; and calculating, (i) an average first time point volume of the organ by averaging the first algorithm-first time point volume and the second mathematically-weighted volume or by averaging the first mathematically-weighted volume and the second algorithm-first time point volume, and (ii) an average second time point volume of the organ by averaging the first algorithm-second time point volume and the second mathematically-weighted volume or by averaging the first mathematically-weighted volume and the second algorithm-second time point volume.

15. The method of claim 14, wherein each of the first plurality of magnetic resonance images and the second plurality of magnetic resonance images includes magnetization-prepared rapid acquisition gradient echo (MPRAGE)-based magnetic resonance images, and fluid-attenuated inversion recover (FLAIR)-based magnetic resonance images.

16. The method of claim 15, wherein the first algorithm is used to calculate the first algorithm-first time point volume and the first algorithm-second time point volume based on the MPRAGE-based magnetic resonance images.

17. The method of claim 15, wherein the second algorithm is used to calculate the second algorithm-first time point volume and the second algorithm-second time point volume based on the FLAIR-based magnetic resonance images.

18. The method of claim 14, further comprising calculating a change in organ volume based on the average first time point volume of the organ and the average second time point volume.

19. The method of claim 14, further comprising:
calculating, using a third algorithm, a third algorithm-first time point volume of the organ at the first time point based on at least one of the first plurality of magnetic resonance images, wherein the third algorithm is different from the first algorithm and the second algorithm; and
calculating, using the third algorithm, a third algorithm-second time point volume of the organ at the second time point based on at least one of the second plurality of magnetic resonance images,
wherein the calculating of the average first time point volume of the organ includes averaging the first algorithm-first time point volume, the second algorithm-first time point volume, and the third algorithm-first time point volume, and the calculating of the average second time point volume of the organ includes averaging the first algorithm-second time point volume, the second algorithm-second time point volume, and the third algorithm-second time point volume.

20. The method of claim 14, wherein each of the first algorithm mathematical weight and the second algorithm mathematical weight is based on at least the image quality score of images associated with the first algorithm and the second algorithm, respectively.

21. A method of calculating a volume of an organ in a patient, the method comprising:
obtaining at least one magnetization-prepared rapid acquisition gradient echo (MPRAGE)-based magnetic resonance image of the organ at each of a first time point and a second time point;
obtaining at least one fluid-attenuated inversion recover (FLAIR)-based magnetic resonance image of the organ at each of the first time point and the second time point;
calculating, using a first algorithm, a first algorithm-first time point volume of the organ at the first time point based on the at least one MPRAGE-based magnetic resonance image obtained at the first time point;
calculating, using the first algorithm, a first algorithm-second time point volume of the organ at the second time point based on the at least one MPRAGE-based magnetic resonance image obtained at the second time point;
calculating, using a second algorithm, a second algorithm-first time point volume of the organ at the first time point based on the at least one FLAIR-based magnetic resonance image obtained at the first time point, wherein the second algorithm is different from the first algorithm;
calculating, using the second algorithm, a second algorithm-second time point volume of the organ at the second time point based on the at least one FLAIR-based magnetic resonance image obtained at the second time point;
applying at least one of (a) a first algorithm mathematical weight to at least one of the first algorithm-first time point volume and the first algorithm-second time point volume, the first algorithm mathematical weight being associated with the first algorithm, to obtain a first mathematically-weighted volume, and (b) a second algorithm mathematical weight to at least one of the second algorithm-first time point volume and the second algorithm-second time point volume, the second algorithm mathematical weight being associated with the second algorithm, to obtain a second mathematically-weighted volume, wherein the first mathematically-weighted volume is a product of the first mathematical weight, and the at least one of the first algorithm-first time point volume and the first algorithm-second time point volume, and the second mathematically-weighted volume is a product of the second algorithm mathematical weight and the at least one of the second algorithm-first time point volume and the second algorithm-second time point volume,
wherein each of the first algorithm mathematical weight and the second algorithm mathematical weight is calculated based on at least one of: an image quality score, a reliability index of the corresponding algorithm, historical data of the corresponding algorithm, a measurement error of the corresponding algorithm, a synchronicity of the corresponding algorithm, a performance of the corresponding algorithm, and a degree of similarity with one or more other brain volume values; and
calculating an average first time point volume of the organ by averaging the first algorithm-first time point volume and the second mathematically-weighted volume or by averaging the first mathematically-weighted volume and the second algorithm-first time point volume; and
calculating an average second time point volume of the organ by averaging the first algorithm-second time point volume and the second mathematically-weighted volume or by averaging the first mathematically-weighted volume and the second algorithm-second time point volume.

22. The method of claim 21, further comprising calculating a change in organ volume based on the average first time point volume and the average second time point volume.

23. The method of claim 21, wherein each of the first algorithm mathematical weight and the second algorithm mathematical weight is based on at least the image quality score of images associated with the first algorithm and the second algorithm, respectively.

* * * * *